United States Patent
Martin et al.

(10) Patent No.: US 8,443,428 B2
(45) Date of Patent: May 14, 2013

(54) WEB BASED ACCESS TO CLINICAL RECORDS

(75) Inventors: Neil A. Martin, Encino, CA (US); Farzad D. Buxey, Marina Del Rey, CA (US); Vesselin Zlatev, Aliso Viejo, CA (US)

(73) Assignees: The Regents of the University of California, Oakland, CA (US); Global Care Quest, Inc., Aliso Viejo, CA (US)

( * ) Notice: Subject to any disclaimer, the term of this patent is extended or adjusted under 35 U.S.C. 154(b) by 455 days.

(21) Appl. No.: 12/495,285

(22) Filed: Jun. 30, 2009

(65) Prior Publication Data

US 2009/0328176 A1 Dec. 31, 2009

Related U.S. Application Data

(60) Provisional application No. 61/077,159, filed on Jun. 30, 2008.

(51) Int. Cl.
*H04L 29/06* (2006.01)

(52) U.S. Cl.
USPC .................................... 726/7; 726/4

(58) Field of Classification Search .......... 726/7, 2, 726/4; 715/781
See application file for complete search history.

(56) References Cited

U.S. PATENT DOCUMENTS

| 7,523,401 | B1 * | 4/2009 | Aldridge .................. 715/760 |
| 2001/0049610 | A1 * | 12/2001 | Hazumi .................... 705/3 |
| 2004/0024616 | A1 | 2/2004 | Spector et al. |
| 2004/0158132 | A1 | 8/2004 | Zaleski |
| 2004/0186746 | A1 * | 9/2004 | Angst et al. .................. 705/3 |
| 2005/0192839 | A1 * | 9/2005 | St. Jacques et al. ........ 705/2 |
| 2006/0010098 | A1 | 1/2006 | Goodnow et al. |
| 2006/0013462 | A1 | 1/2006 | Sadikali |
| 2007/0043596 | A1 | 2/2007 | Donaldson et al. |
| 2007/0233519 | A1 | 10/2007 | Lorsch |
| 2008/0163066 | A1 * | 7/2008 | Gu et al. .................. 715/738 |
| 2009/0021790 | A1 * | 1/2009 | Krovitz et al. ........... 358/1.18 |

FOREIGN PATENT DOCUMENTS

| JP | 2001325372 A | 11/2001 |
| JP | 2004178435 A | 6/2004 |
| JP | 2004243126 A | 9/2004 |
| JP | 2007052800 A | 3/2007 |
| JP | 2009514108 A | 4/2009 |
| WO | 2007053468 A2 | 5/2007 |

OTHER PUBLICATIONS

European Search Report; Application No. EP 09 16 4224; Mar. 11, 2011; 11 pages.

* cited by examiner

*Primary Examiner* — Ali Abyaneh
(74) *Attorney, Agent, or Firm* — St. Onge Steward Johnston & Reens LLC

(57) ABSTRACT

A system and method for providing access to clinical data over the Internet. The system includes a server, and a database in communication with the server. The database stores clinical data sets. The system further includes a thin client, a communication link between the server and the Internet, and a communication link between the thin client and the Internet. Software executing on the server receives a request for one or more clinical data sets, retrieves the requested clinical data sets, and transmits the clinical data sets to the thin client.

13 Claims, 8 Drawing Sheets

FIG. 5A

WEB BASED ACCESS TO CLINICAL RECORDS

CROSS-REFERENCE TO RELATED APPLICATIONS

The present application claims the benefit under 35 U.S.C. §119(e) of the Provisional Patent Application Ser. No. 61/077,159 filed Jun. 30, 2008 which is herein incorporated by reference.

This Application is related to U.S. patent application entitled "Drill Down Clinical Information Dashboard," filed on Feb. 24, 2008 and having application Ser. No. 12/036,281. That application is incorporated by reference herein.

This Application is related to U.S. patent application entitled "Intelligent Dashboard," filed on Feb. 24, 2008 and having application Ser. No. 12/036,287. That application is incorporated by reference herein.

FIELD OF THE INVENTION

The invention relates to the access of clinical data. Specifically, the invention relates to systems and methods for accessing clinical data and records via the web using a thin client.

BACKGROUND OF THE INVENTION

Clinical data in hospitals and other medical facilities is often stored in a central server or set of servers located on-site at the facility. The central server is primarily accessed via computer terminals at the facility. These computer terminals are referred to a thick clients because data retrieved from the central server is processed on the computer terminal. The data stored on the system is acquired from a multitude of sources, such as the hospital's information system, billing system, and other, more specialized, data repositories.

A disadvantage of such known systems is that it is inconvenient for physicians and other medical staff working at the hospital to access clinical data stored on the central server or servers because they must log on to an on-site computer terminal to view the clinical data.

Another disadvantage of such known systems is that software for processing and receiving the clinical data executes on each on-site computer terminal. Such a system is expensive to maintain because each computer terminal must be addressed individually.

Another disadvantage of such known systems is that they do not enable a person outside the medical staff to access clinical data stored on the system. Patients, for example, cannot access their own clinical data.

Another disadvantage of such known systems is that they do not allow a physician who has referred a patient to the hospital where the patient's data is stored to access the data stored on the system.

There is a desire therefore for a system and method for providing access to clinical data that overcomes the limitations of the prior art.

SUMMARY OF THE INVENTION

It is accordingly an object of the present invention to provide a system and method that that overcomes the limitations of the prior art.

It is another object of the present invention to provide a system and method that provides hospital staff and physicians access to medical data from any electronic device connected to the Internet, or other network.

It is yet another object of the present invention to provide a web-based client to allow for the external viewing of medical data located on a hospital server.

It is another object or the present invention to provide a system and method that provides patient access to clinical data from any electronic device connected to the Internet, or other network. In some embodiments of the present invention patient access is limited to clinical data related to the patient.

It is yet another object of the present invention to provide a system and method that allows a physician, for example a referring physician, to access clinical data stored on the hospital server, thereby providing wide access to the system. In some embodiments of the present invention physician access is limited to clinical data related to one or more patients of the physician.

It is yet another embodiment of the present invention to employ tailored limitations and restrictions of access to individual patients or groups of patients based on patient permissions. In such embodiments, the central data server is no longer an insulated intramural closed system that neither patients nor referring physicians have access to.

It is yet another object of the present invention to provide a system and method that displays clinical data stored on a central hospital server to a thin client (e.g., desktop, notebook, tablet PC, handheld device, etc.). A thin client in some embodiments is a device that primarily handles input (e.g., user interaction) and output (e.g., displaying), while data processing is done on a separate server remote from the thin client. This is as opposed to a thick client, in which processing is done on the thick client device itself. While some of the devices listed above (desktop, notebook, etc.) can also act as thick clients, in some embodiments these devices act as thin clients.

It is yet another object of the present invention to provide a system and method for access to centrally stored clinical data wherein maintenance of the data processing software need only be implemented on software executing on the server.

It is yet another object of the present invention to provide a system and method for the display clinical data stored on a central hospital server on a browser on a thin client, wherein the interface within the browser allows the creation of multiple windows or panes which can be individually sized and individually positioned within the browser. In some embodiments, the number of individual panes can vary from one or two up to eight or more. The panes are variably sized in some embodiments, and multiple windows can have differing sizes.

It is yet another object of the present invention to provide a central server facility that servers multiple hospitals in multiple geographic locations, thereby improving the efficiency of server maintenance and upgrading, and application upgrading at both the server level and the client level.

It is yet another object of the present invention to employ remote hosting to hospitals on a subscription basis that allows hospitals to forego the high costs of hardware installation and on-site maintenance.

These and other objects of the present invention are achieved by a system and method for providing web access to clinical data including a server, a database in communication with the server, the database having a plurality clinical data sets. The system further includes a thin client, a communication link between the server and the Internet, and a communication link between the thin client and the Internet. Software executing on the server receives a request for one or more clinical data sets, retrieves the requested clinical data sets, and transmits the clinical data sets to the thin client.

In some embodiments of the present invention, software executing on the server generates a dashboard for display on the thin client. The dashboard comprises one of more window panes for displaying the clinical data sets on the thin client.

In some embodiments, because the application that is provided to the thin client runs on the server, modifications to the application need only be implemented in the central location rather than on each thin client device. This greatly simplifies the updating and maintenance of the application. Some embodiments do not permit caching of any data on the thin client. Other embodiments only permit the standard sort of caching that is associated with typical web applications and allowed by standard web browsers like Firefox and Internet Explorer.

In some embodiments, the web-based application allows patients to see their own records without being required to download software onto their computer. Such embodiments are restricted such that the patient (in contrast to healthcare workers associated with the hospital or other facility) will have access only to their own personal medical record and not to the entire list of patients in the hospital. Some embodiments associate a particular patient's password with that particular patient's medical record, and only allow the patient to view that particular record. In such embodiments, patients do not have the ability to browse other medical records within the facility. This security step is critical for privacy and HIPAA (Health Insurance Portability and Accountability Act) compliance.

In some embodiments, the web access similarly facilitates the reviewing of patient records by referring physicians who are not on-site in the hospital or even on the medical staff of the hospital. Such physicians might want to easily access the records of patients who they referred to the hospital. Some embodiments restrict access of a particular physician to only patients that have given permission for that particular physician to view their records. Accordingly, physicians who are not on the medical staff will not have the ability to view all of the medical records within the facility at will in such embodiments, but rather only those of the patients who have granted them permission to see their records. The ability of patients and referring physicians to easily view pertinent medical records within a hospital system is an extension of that system that will bring the healthcare infrastructure a step closer to being universally accessible.

In some embodiments, the server that runs the web-based application is hosted remotely rather than installed in the hospital. In such embodiments, all that is required is a network (e.g., Internet) link between the central server facility and the client hospital, which can be geographically distant. In some embodiments, the central server facility serves multiple hospitals in multiple geographic locations, thereby improving the efficiency of server maintenance and upgrading, and application upgrading at both the server level and the client level. Some embodiments that employ remote hosting provide the remote hosting to hospitals on a subscription basis that allows the hospitals to forego the high costs of hardware installation and on-site maintenance.

Some embodiments allow patients and referring physicians to view patient hospital records, thereby providing wide access to the system. Some embodiments employ tailored limitations and restriction of access to individual patients or a group of patients based on patient permissions. In such embodiments, the central data server is no longer an insulated intramural closed system that neither patients nor referring physicians have access to.

These and other objects and advantages of the present invention will become more apparent from the following detailed description considered with reference to the accompanying drawings.

BRIEF DESCRIPTION OF THE DRAWINGS

FIG. 5A illustrates a dashboard for display on a thin client according to one embodiment of the present invention.

DETAILED DESCRIPTION OF THE INVENTION

Figure 1:
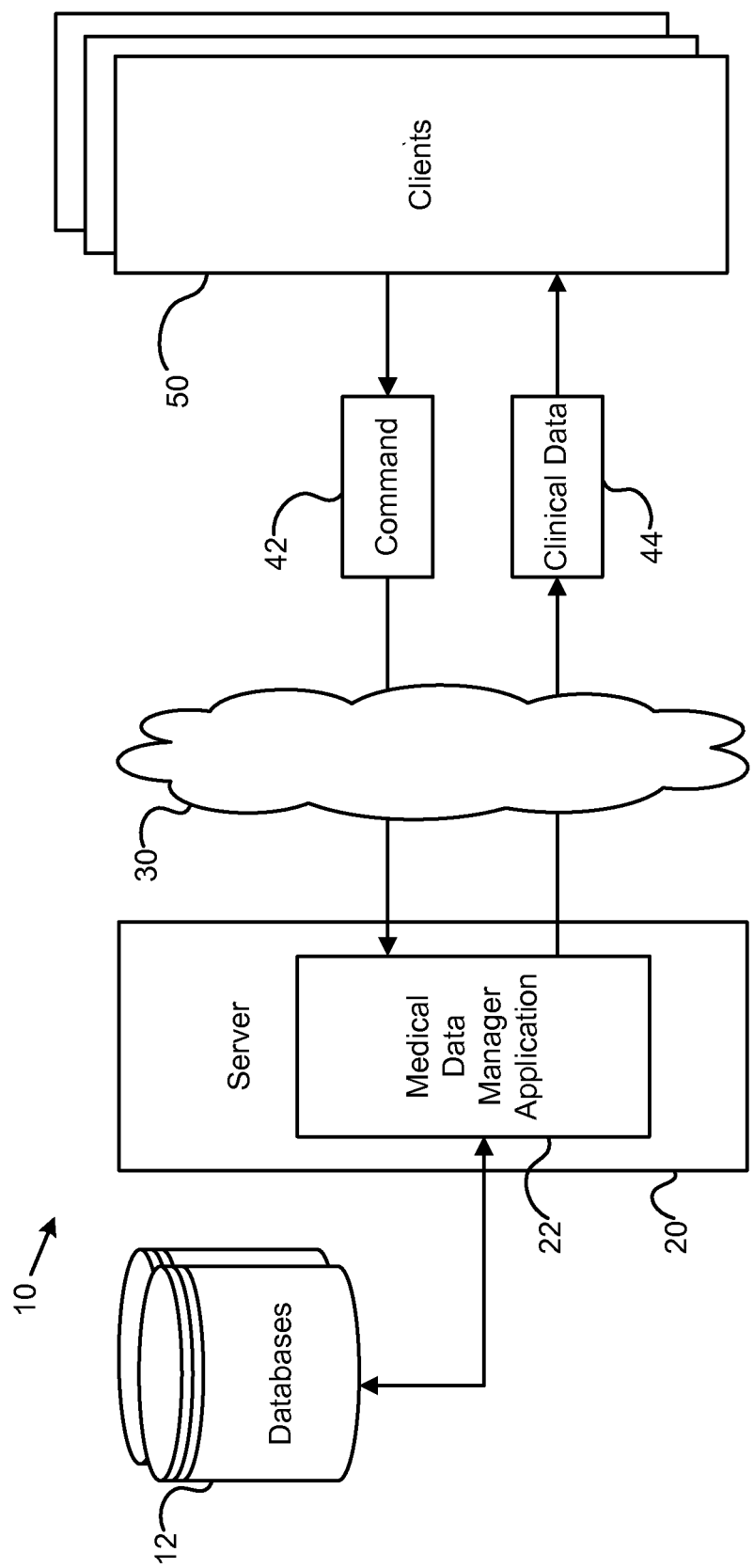
FIG. 1 illustrates a system and method for providing web based access to clinical records according to one embodiment of the present invention.

FIG. 1 illustrates a system 10 for providing access to clinical data over a network according to one embodiment of the present invention. The system 10 includes a server 20 accessible by one or more thin clients 50 via a communication network 30. In some embodiments, the server 20 may be a personal computer that is accessible (via the communications network 30 or directly) by one or more thin clients 50. In other embodiments the server 20 may be a plurality of servers 20 connected together. In some embodiments the communication network 30 is a communication link over the Internet, and in other embodiments the communication network 30 may be a communication link over a private or closed network.

The system 10 further includes one or more databases 12 for storing clinical data. Clinical data may include any data related to the treatment and care of a patient, for example data related to the condition of a patient, billing and payment history, and a patient's medical history. For the purposes of this application clinical data also refers to severity scores, and data trends calculated to monitor and evaluate one or more patients. Clinical data is collected through a variety of systems and methods and stored in the database 12 connected to the server 20. The database 12 provides the system 10 with clinical data for a number of patients.

Figure 2:
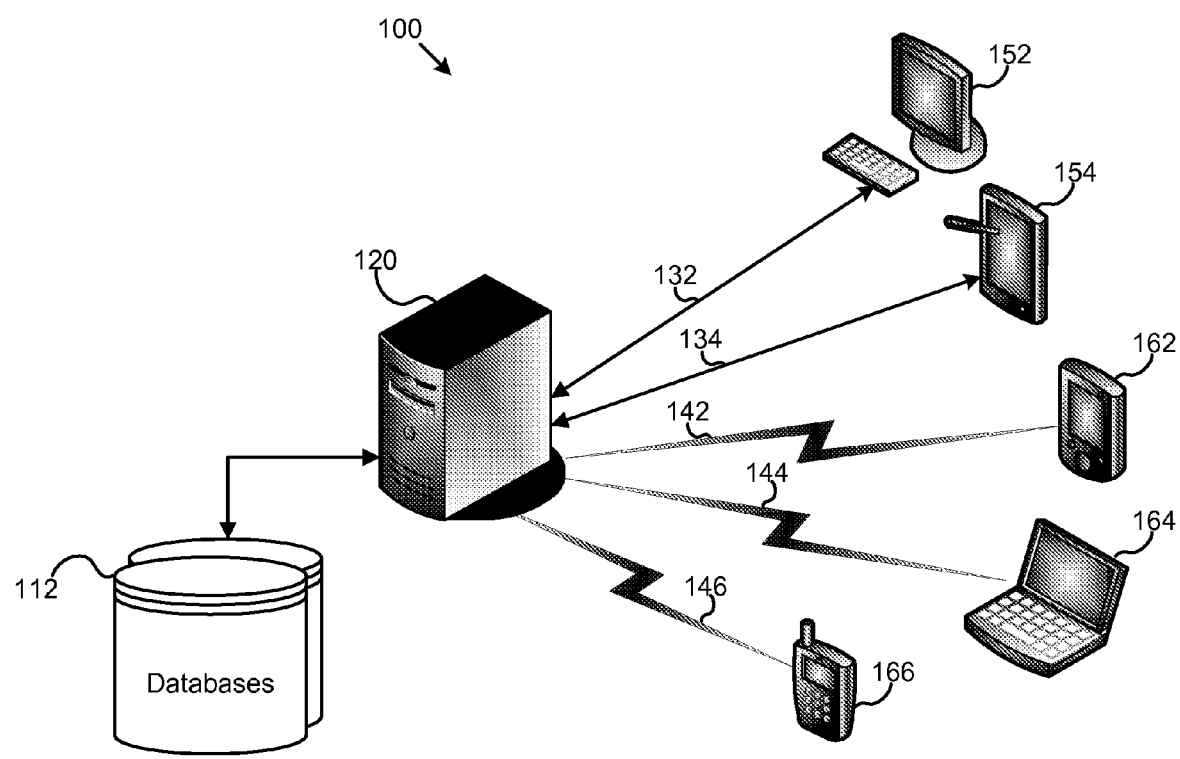
FIG. 2 illustrates a system for providing web based access to clinical records according to one embodiment of the present invention.

In reference to FIG. 2 an embodiment of the present invention is shown. A thin client 50 may include, but is not limited to, a desktop computer 152, a notebook computer 164, a tablet computer 154, a personal digital assistant 162, and a mobile phone 166. A thin client 50 in some embodiments is a device that primarily handles input (e.g., user interaction) and output (e.g., displaying), while processing is done on a separate server. This is as opposed to a thick client, in which processing is done on the client device itself. While some of the devices listed above (desktop, notebook, etc.) can also act as thick clients, in some embodiments these devices act as thin clients 50. Thin clients 152, 154 are in communication with the server 120 via private communication networks 132, 134 respectively. Thin clients 162, 164, 166 are in communication with the server 120 via public communication networks 142, 144, 146 respectively, for example the Internet.

In further reference to the embodiment shown in FIG. 1 the thin client 50 is in communication with the server 20 via a communication network 30. In some embodiments the thin client 50 is connected to the Internet via a communication link. The thin client 50 may include a web browser for communicating with said server 20 via said communication network 30. It should be understood that in some embodiments of the present invention the thin client 50 is in communication with the server 20 via a private network. It should further be understood that in some embodiments of the present invention one or more thin clients 50 are in communication with the server 20 via a wireless network.

The server 20 includes software for processing clinical data stored in the database 12. In reference to FIG. 1 the software executing on the server 20 is referred to as a Medical Data Manager Application 22. It should be understood that the Medical Data Manager Application 22 includes a plurality of software modules for processing clinical data stored in the database 12, and that the Medical Data Manager Application 22 may be referred to throughout this description as software 22.

In further reference to FIG. 1, software 22 executing on the server 20 receives a command 42 from said thin client 50. In the embodiments shown in FIG. 1 the command 42 is a request for clinical data 44. It should be understood that the server 20 may receive many different commands, for example a command to process clinical data, or a command to present clinical data in a different manner. Software 22 executing on the server 20 retrieves the requested clinical data 44 from the database 12 in response to the command 42. Software 22 executing on the server 20 transmits the requested clinical data 44 to the thin client 50 via the network communication link 30. The requested clinical data 44 is displayed on a user interface on the thin client 50.

Figure 5A:
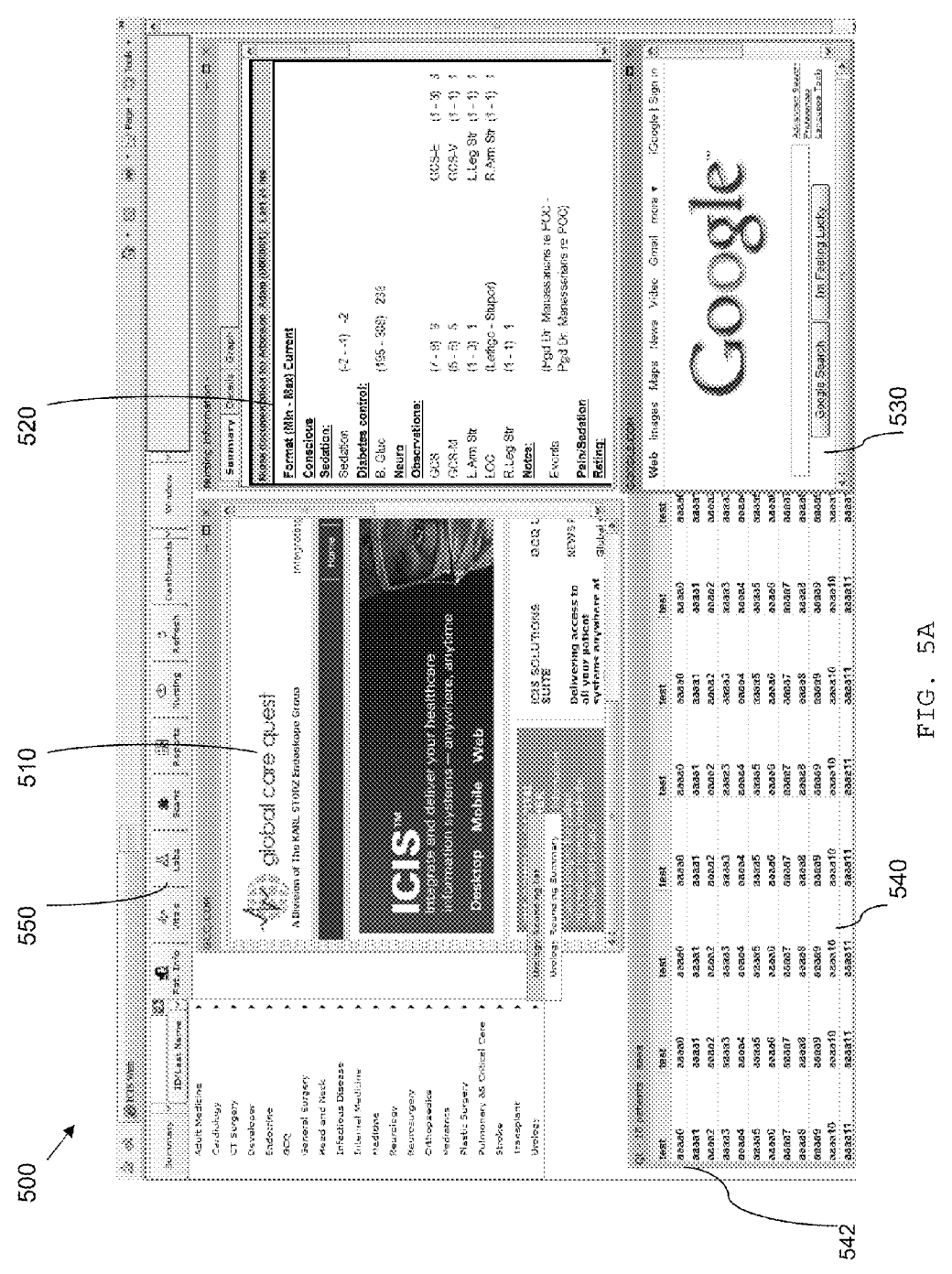
Figure 5B:
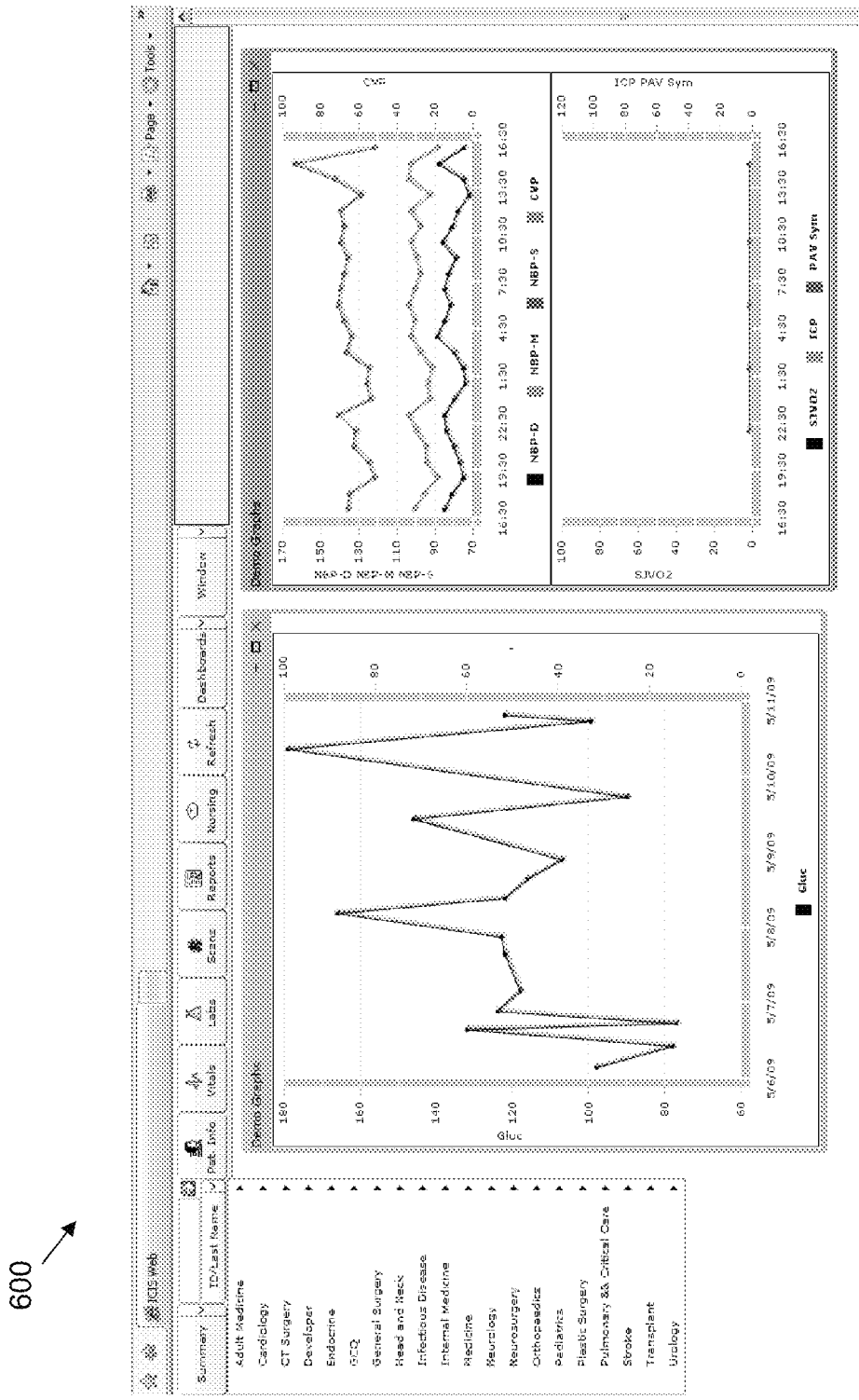
FIG. 5B illustrates a dashboard for display on a thin client according to one embodiment of the present invention.
Figure 5C:
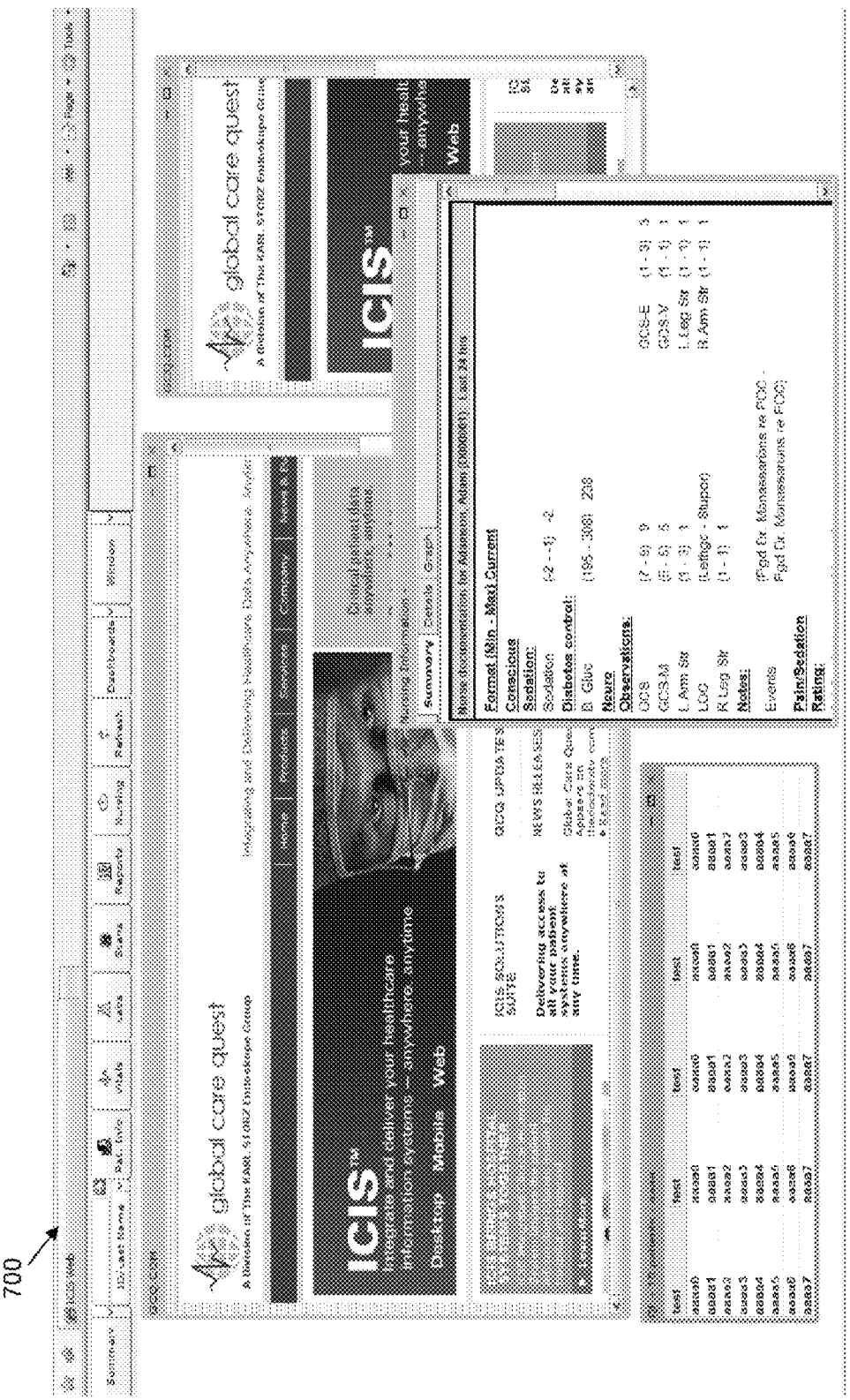
FIG. 5C illustrates a dashboard for display on a thin client according to one embodiment of the present invention.
Figure 5D:
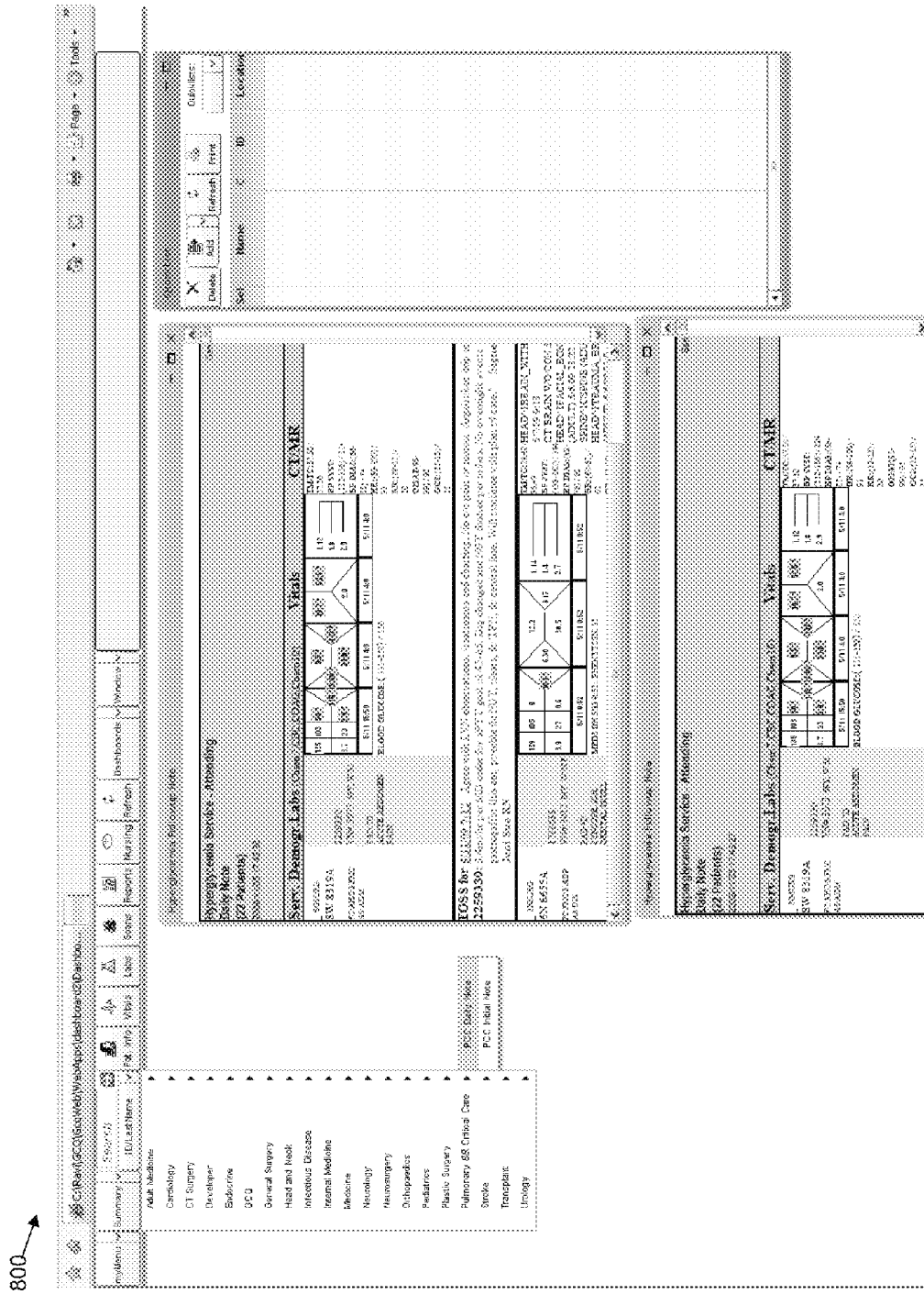
FIG. 5D illustrates a dashboard for display on a thin client according to one embodiment of the present invention.

In some embodiments of the present invention the system includes software 22 executing on the server 20 for generating a user interface (or dashboard). In reference to FIGS. 5A-D various examples of the user dashboards 500, 600, 700, 800 are shown. The thin client 50 displays the dashboard 500 generated by software 22 executing on the sever 20. The dashboard 500 is typically displayed in the user interface of the thin client 50. For example the dashboard 500 may be displayed inside a web browser running on the thin client 50. Each dashboard 500, 600, 700, 800 includes multiple window panes, such as the window panes 510, 520, 530, 540 shown on dashboard 500 in FIG. 5A. The various window panes of the dashboards display clinical data. For instance, the window pane 520 shows clinical data regarding a first patient.

In some embodiments, the dashboard includes a patient list window, such as the patient list window 540 of dashboard 500. The patient list window 540 provides a list of the patients, recorded clinical data regarding each patient, computed scores generated from patient clinical data, and trends associated with the recorded data and generated scores. In some embodiments, the patient list window 540 is editable, selectable, or clickable.

In reference to the embodiment shown in FIG. 5A, the dashboard 500 further includes a menu bar 550. The menu bar 550 has one or more menu options, for example vitals, labs, scans, and nursing. When a menu bar option is selected (via appropriate input on the thin client 50), the menu "pulls down", revealing a list of menu items or options. These options enable the user to perform various actions within the dashboard 500 and allow the user to request one or more clinical data sets. In some embodiments, a user can configure a dashboard 500. For example, the user can configure one or more of a size of a window pane, the number of window panes, and the type of data displayed in a window pane. The system 10 can further save a dashboard configuration for later use.

In reference to FIG. 1 software 22 executing on the server 20 generates a first dashboard 500 having a first plurality of window panes 510, 520, 530, 540. Software 22 executing on the server 20 transmits the first dashboard 500 to a thin client 50 for display on the thin client 50. In some embodiments of the present invention software executing 22 on the server 20 displays the clinical data 44 in one or more of the first plurality of window panes 520 of the first dashboard 500. For example, in reference to FIG. 5A the system 10 displays the dashboard 500 on a thin client 50. A user of the thin client 50 may request clinical data, for example, by selecting a patient name on the patient list window pane 540. The software 22 executing on the server 20 receives the request 42 for the clinical data, retrieves the requested clinical data 44 from the database 12, and transmits the requested clinical data 22 to the thin client 50 for display in a window pane 520 of the dashboard 500.

In some embodiments of the present invention a first dashboard 500 generated by software 22 executing on the server 20 is displayed on the thin client 50. The user of the thin client 50 requests clinical data via an input on the first dashboard 500. Software 22 executing on the server 20 receives the request, and retrieves the requested clinical data 44. Software 22 executing on the server 20 then generates a second dashboard 600 having a second plurality of window panes and transmits the second dashboard 600 to the thin client 50 for display on the thin client 50. In some embodiments the first dashboard 500 includes a link 542, for example a patient name in the patent list window pane 540. When the link 542 is activated, for example by a user input at the thin client 50, software 22 executing on the server 20 generates a second dashboard 600, and includes clinical data 44 in one or more window panes on the second dashboard 600, wherein the clinical data 44 is related to the patient associated with the link 542. In this way the user of a thin client 50 can toggle between a general dashboard 500 in which clinical information related to a plurality of patients is displayed, to a more specialized dashboard 600 in which additional patient specific clinical information is displayed.

In other embodiments of the present invention a first dashboard having a first set of window panes displays a first set of clinical data related to a first aspect of a patient, for example general clinical data associated with the patient. A second a second dashboard having a second set of plurality of windows displays clinical data related to a second aspect of a patient, for example clinical data related to a specific condition for which medical staff intends to treat. It should be understood that in some embodiments the first and second dashboards may display identical clinical data, while in other embodiments the first and second dashboards display different clinical data.

In some embodiments software executing the server 20 provides a web browser in a window pane 530 of the dashboard 500. A user of the thin client 50 can access the World Wide Web through the browser provided in the window pane 530. For example, a user accessing the system through a thin client 50 connected to a private network or closed network can access the World Wide Web via the browser window pane 530.

In some embodiments, the web-based application allows doctors, patients, and other individuals located outside of a hospital to access clinical data sets stored on the system. In such embodiments it is preferred that access to clinical data is restricted to persons with authorization to access such clinical data. For example, a patient is authorized to access her own clinical data, but is restricted from accessing clinical data of other patients. Such embodiments are restricted such that the patient (in contrast to healthcare workers associated with the hospital) have access only to their own personal clinical data and not to the entire list of patients in the hospital. In other embodiments a referring doctor will have access only to patients of the doctor. This security step is critical for privacy and HIPAA (Health Insurance Portability and Accountability Act) compliance.

Figure 3:
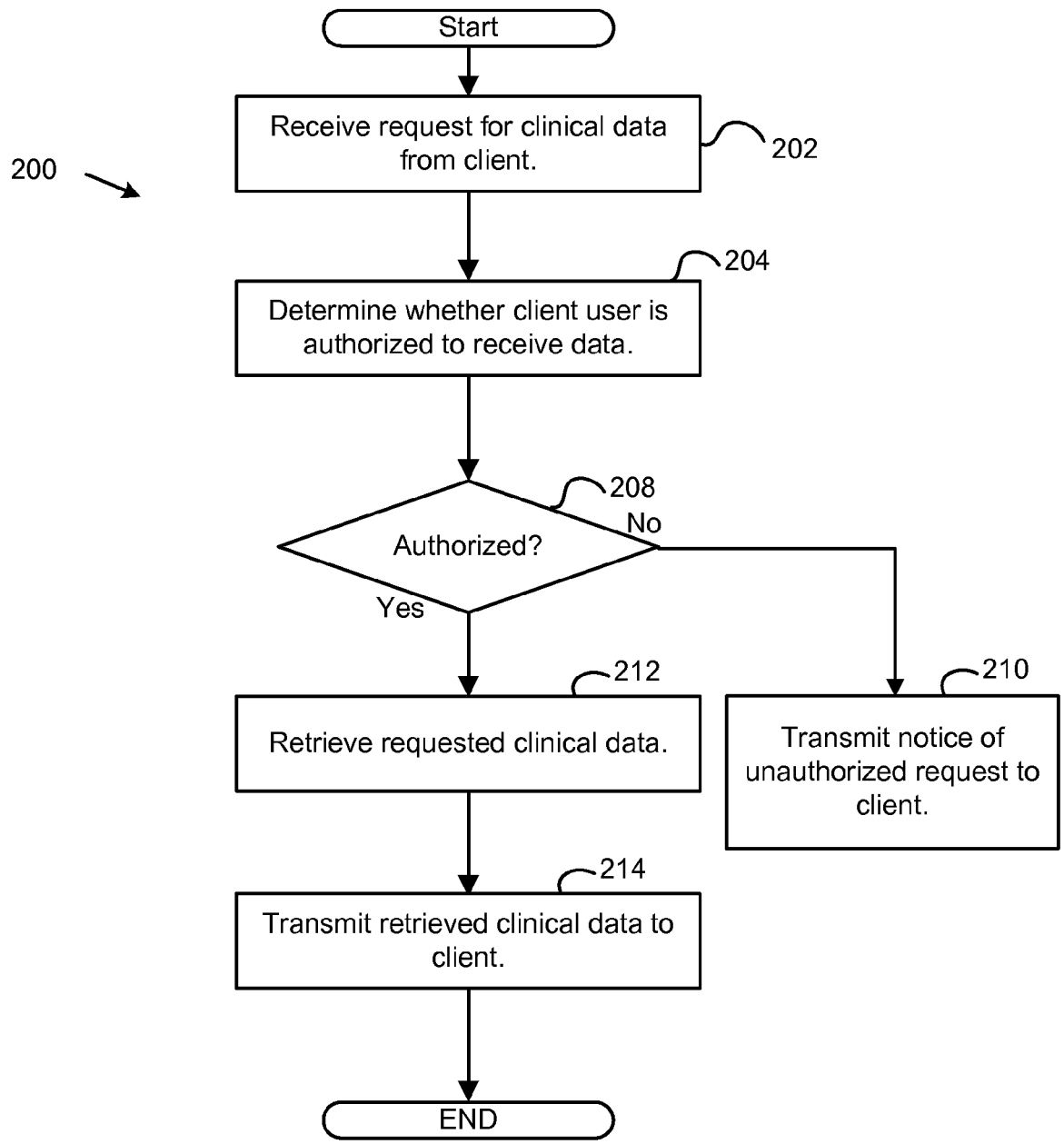
FIG. 3 illustrates a method according to one embodiment of the present invention.

In reference to FIG. 3, a method for restricting access to clinical data is illustrated. First, the server receives a clinical data request from a thin client 202. Each clinical data request is associated with a unique identifier related to the one or more of thin client through which the request was made, or the user making the request through the thin client. Further, the clinical data stored in the database 12 is also associated with one or more identifies. Software 22 executing on the server 20 receives the clinical data request from the thin client. Software 22 executing on the server 20 determines whether one or more of the thin client 50 and thin client user are authorized to access the clinical data requested based on one or more of the unique identifiers. If the system determines that it is an authorized request, software executing on the server will retrieve the requested data 212, and transmit the clinical data to the thin client 214. If the system determines that it is an unauthorized request, software executing on the server will generate a notice of unauthorized request, transmit the notice of unauthorized request to the thin client 210, and block access to the requested data. It should be understood that many different variations of determining clinical data access are possible, and the above description is intended for illustration purposes only. For example, a data authorization protocol may vary depending on the system, the number of users, the type of user, and the location of the user among others.

Figure 4:
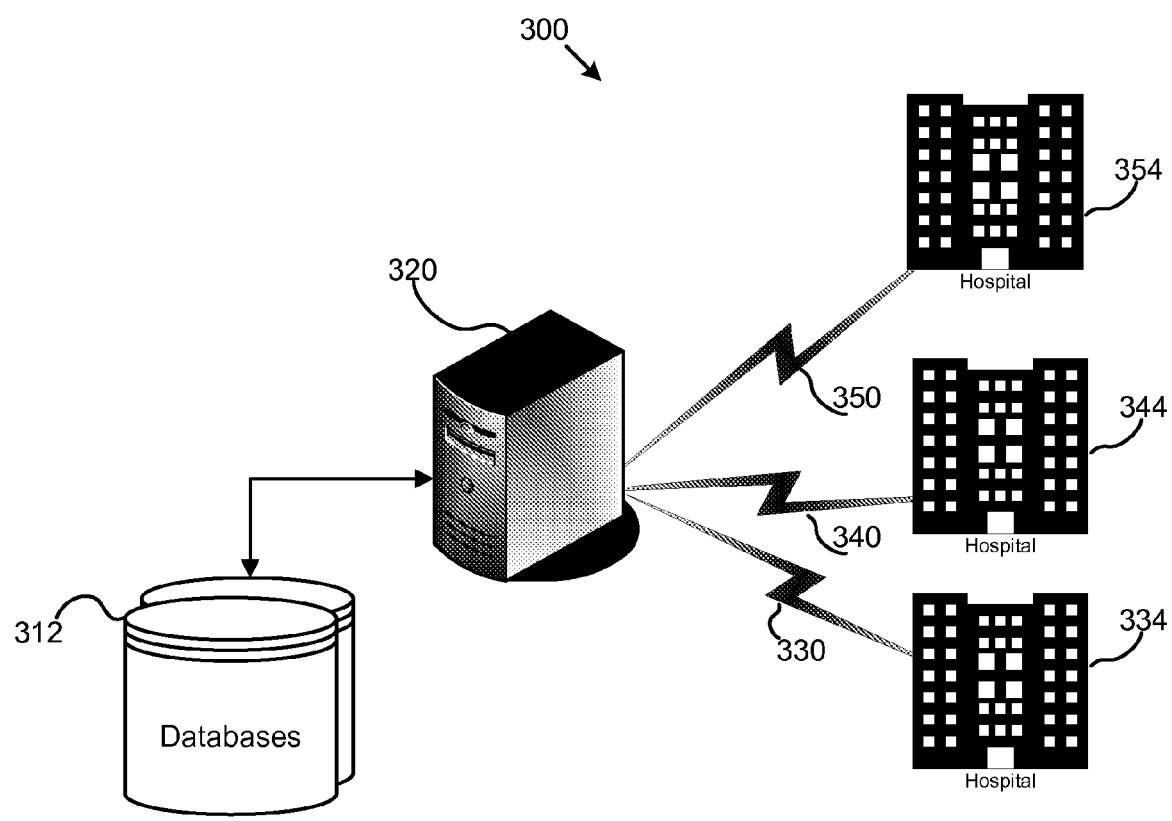
FIG. 4 illustrates a system for providing web based access to clinical records according to one embodiment of the present invention, wherein a central server provides clinical data access over the Internet to one or more hospitals in a geographical location distinct from the server.

In reference to FIG. 4, an alternative embodiment of the present invention is illustrated wherein the server that runs the web-based application is in a geographic location remote from one more medical care facilities. For example the server location may in a different city, county, state or country. In this embodiment the server 320 is located in a geographical location remote from the hospital 354, 344, 334. The server 320 and associated database 312 fulfill data storage and processing for a plurality of hospitals. A user at a hospital accesses data stored on the server. The server processes the data and transmits the data to the hospital. In some embodiments, a hospital may also maintain a local network. Some embodiments that employ remote hosting provide the remote hosting to hospitals on a subscription basis that allows the hospitals to forego the high costs of hardware installation and on-site maintenance.

Although the invention has been described with reference to a particular arrangement of parts, features and the like, these are not intended to exhaust all possible arrangements or features, and indeed many modifications and variations will be ascertainable to those of skill in the art.

What is claimed is:

1. A system for providing access to clinical data, the system comprising:
   a server;
   at least one database in communication with said server, said database comprising a plurality clinical data sets;
   a client;
   a communication link between said server and the Internet;
   a communication link between said client and the Internet;
   software executing on said server for receiving a request for one or more clinical data sets;
   software executing on said server for determining whether the client is authorized to access the one or more clinical data sets requested based on one or more unique identifiers;
   software executing on said server for retrieving said one or more clinical data sets in response to said request;
   software executing on said server for transmitting said one or more clinical data sets to said client if the client is authorized to access the one or more clinical data sets;
   software executing on said server for transmitting a notice of unauthorized request to the client and blocking access to the one or more clinical data sets if the client is unauthorized to access the one or more clinical data sets;
   software executing on said server for generating a first interface comprising a first plurality of window panes, wherein at least one of said first plurality of window panes displays said one or more clinical data sets, and wherein said first set of plurality of windows displays a first clinical data set related to f first aspect of a patient;
   software executing on said server for transmitting said first interface to said client for display on said client;
   software executing on said server for generating a second interface comprising a second plurality of window panes, wherein said second set of plurality of windows displays a second clinical data set related to a second aspect of said patient; and
   software executing on said server for transmitting said second interface to said client for display on said client,
   wherein said first interface further comprises a link that causes said second interface to be displayed on said client when an item is selected in at least one of the first plurality of window panes, and
   wherein a user of said client is able to toggle between said first interface and said second interface.

2. The system of claim 1 wherein said first aspect of the patient and said second aspect of the patient are different.

3. The system of claim 1, further comprising:
   software executing on said server for reconfiguring said first interface by adjusting one or more of a size of a window pane, a number of a window panes, and a type of data displayed in a window pane.

4. The system of claim 3, further comprising:
   software executing on said server for storing said reconfigured first interface.

5. The system of claim 4 wherein said first interface is reconfigured in response to a command received from said client.

6. The system of claim 1, wherein at least one of said first plurality of first window panes displays a list comprising a plurality of patients.

7. The system of claim 6, wherein said software receives a request for one or more clinical data sets related to at least one patient of said plurality of patients.

8. The system of claim 1, further comprising:
   software executing on said server for providing a web browser for display in one of said first plurality of window panes;
   wherein a user of said client can access the World Wide Web through said web browser.

9. A system for providing access to clinical data over the Internet, said system comprising:
   a server;
   at least one database in communication with said server, said database comprising a plurality of clinical data sets;
   a thin client;
   a communication link between said server and the Internet;
   a communication link between said client and the Internet;

software executing on said server for receiving a request for a first clinical data set;

software executing on said server for determining whether the client is authorized to access the one or more clinical data sets requested based on one or more unique identifiers;

software executing on said server for retrieving said first clinical data set in response to said request;

software executing on said server for generating a first interface comprising a first plurality of window panes for display on said client, wherein said first set of plurality of windows displays a first clinical data set related to a first aspect of a patient;

software executing on said server for transmitting said first interface to said client if the client is authorized to access the one or more clinical data sets;

software executing on said server for generating a second interface comprising a second plurality of window panes, wherein said second set of plurality of windows displays a second clinical data set related to a second aspect of said patient;

software executing on said server for transmitting said second interface to said client for display on said client;

wherein said first interface further comprises a link that causes said second interface to be displayed on said client when an item is selected in at least one of the first plurality of window panes; and software executing on said server for transmitting a notice of unauthorized request to the client and blocking access to the one or more clinical data sets if the client is unauthorized to access the one or more clinical data sets, wherein said first clinical data set is displayed in a window pane of said first plurality of window panes, wherein a user of said client is able to toggle between said first interface and said second interface, and wherein said first aspect of said patient and said second aspect of said patient are different.

10. The system of claim 9 further comprising:

software executing on said server for providing a web browser for display in a second window pane of said plurality of window panes;

wherein a user of said client can access the World Wide Web through said web browser.

11. A method for providing access to clinical data over the Internet, said method comprising the steps of:

providing a server;

providing at least one database in communication with said server, said database comprising a plurality of clinical data sets;

providing a thin client;

providing a communication link between said server and the Internet;

providing a communication link between said client and the Internet;

receiving a request for a first clinical data set related to a first aspect of a patient;

determining whether a user of the client is authorized to access the one or more clinical data sets requested based on one or more unique identifiers;

retrieving said first clinical data set in response to said request if the client is authorized to access the one or more clinical data sets, generating a notice of unauthorized request to the client, transmitting a notice of unauthorized request to the client, and blocking access to the one or more clinical data sets if the client is unauthorized to access the one or more clinical data sets;

generating an interface comprising a plurality of window panes for display on said client, said plurality of window panes displaying said first clinical data set;

generating a second interface comprising a second plurality of window panes for display on said client, said second plurality of window panes displaying a second clinical data set related to a second aspect of a patient;

transmitting said interface to said client;

transmitting said second interface to said client;

displaying said first clinical data set in a first window pane of said plurality of window panes on said interface;

displaying said second clinical data set in a second window pane of said plurality of window panes on said second interface.

12. The method of claim 11 further comprising the steps of:

providing a web browser for display in a second window pane of said plurality of window panes;

wherein a user of said client can access the World Wide Web via said web browser.

13. The method of claim 11 further comprising the steps of:

providing a list of a plurality of patients in a second window pane;

retrieving a clinical data set related to one of said plurality of patients.

* * * * *